United States Patent
Bentley et al.

(10) Patent No.: US 8,008,435 B2
(45) Date of Patent: Aug. 30, 2011

(54) POLYMER STABILIZED NEUROPEPTIDES

(75) Inventors: Michael David Bentley, Huntsville, AL (US); Michael James Roberts, Madison, AL (US)

(73) Assignee: Nektar Therapeutics, San Francisco, CA (US)

(*) Notice: Subject to any disclaimer, the term of this patent is extended or adjusted under 35 U.S.C. 154(b) by 513 days.

(21) Appl. No.: 10/647,561

(22) Filed: Aug. 25, 2003

(65) Prior Publication Data
US 2004/0038899 A1 Feb. 26, 2004

Related U.S. Application Data

(63) Continuation of application No. 09/678,997, filed on Oct. 4, 2000, now abandoned.

(60) Provisional application No. 60/166,589, filed on Nov. 19, 1999.

(51) Int. Cl.
*A61K 38/00* (2006.01)

(52) U.S. Cl. ........................................ 530/345

(58) Field of Classification Search ................ None
See application file for complete search history.

(56) References Cited

U.S. PATENT DOCUMENTS

| | | | |
|---|---|---|---|
| 4,179,337 A | 12/1979 | Davis et al. | |
| 4,462,941 A | 7/1984 | Lee et al. | |
| 4,468,383 A | 8/1984 | Rodbard et al. | |
| 4,518,711 A | 5/1985 | Hruby et al. | |
| 4,684,624 A | 8/1987 | Hosobuchi et al. | |
| 4,902,505 A | 2/1990 | Pardridge et al. | |
| 5,017,689 A | 5/1991 | Hruby et al. | |
| 5,286,637 A | 2/1994 | Veronese et al. | |
| 5,326,751 A | 7/1994 | Haaseth et al. | |
| 5,359,030 A | 10/1994 | Ekwuribe | |
| 5,428,128 A | 6/1995 | Mensi-Fattohi et al. | |
| 5,442,043 A | 8/1995 | Fukuta et al. | |
| 5,629,384 A | 5/1997 | Veronese et al. | |
| 5,631,322 A | 5/1997 | Veronese et al. | |
| 5,670,477 A | 9/1997 | Poduslo et al. | |
| 5,681,811 A | 10/1997 | Ekwuribe | |
| 5,833,988 A | 11/1998 | Friden | |
| 5,932,462 A | 8/1999 | Harris et al. | |
| 5,948,389 A | 9/1999 | Stein | |
| 5,990,237 A | 11/1999 | Bentley et al. | |
| 6,024,977 A | 2/2000 | Yatvin et al. | |
| 6,046,305 A | 4/2000 | Choi | |
| 6,309,633 B1 | 10/2001 | Ekwuribe et al. | |
| 6,362,254 B2 | 3/2002 | Harris et al. | |
| 6,433,135 B1 | 8/2002 | El-Tayar et al. | |
| 6,552,170 B1 | 4/2003 | Thompson et al. | |
| 6,703,381 B1 | 3/2004 | Ekwuribe et al. | |
| 6,899,867 B2 | 5/2005 | Bentley et al. | |
| 7,056,500 B2 | 6/2006 | Bentley et al. | |
| 2002/0013266 A1 | 1/2002 | Bentley et al. | |
| 2002/0019340 A1 | 2/2002 | Bentley et al. | |
| 2003/0139346 A1 | 7/2003 | Bentley et al. | |
| 2003/0144207 A1 | 7/2003 | Bentley et al. | |
| 2004/0038899 A1 | 2/2004 | Bentley et al. | |

FOREIGN PATENT DOCUMENTS

| | | |
|---|---|---|
| WO | WO91/16355 | 10/1991 |
| WO | WO 91/16929 A | 11/1991 |
| WO | WO 95/00162 A | 1/1995 |
| WO | WO96/03984 | 2/1996 |
| WO | WO98/52415 | 11/1998 |
| WO | WO 00/78302 A1 | 12/2000 |
| WO | WO 01/12230 A1 | 2/2001 |
| WO | WO 01/19406 A2 * | 3/2001 |

OTHER PUBLICATIONS

Inada, et al, "Modification of Proteins with Polyethylene Glycol Derivatives," Methods in Enzymology, (1994), vol. 242, 65-90.*
Delgado C, Francis GE, Fisher D., "The uses and properties of PEG-linked proteins," Crit Rev Ther Drug Carrier Syst. 1992;9(3-4):249-304.*
Wu D, Pardridge WM., "Neuroprotection with noninvasive neurotrophin delivery to the brain," Proc Natl Acad Sci U S A Jan 5, 1999;96(1):254-9.*
Delgado C, Francis GE, Fisher D., "The uses and properties of PEG-linked proteins," Crit Rev Ther Drug Carrier Syst. 1992;9(3-4):249-304.*
Wu D, Pardridge WM., "Neuroprotection with noninvasive neurotrophin delivery to the brain," Proc Natl Acad Sci U S A. Jan 5, 1999;96(1 ):254-259.*
Sakane et al., "Carboxyl-directed Pegylation of Brain-derived Neurotrophic Factor Markedly Reduces Systemic Clearance with Minimal Loss of Biological Activity," Pharm Res., 14(8):1085-1091 (1997).*
Abbruscato TJ, et al, "Blood-to-central nervous system entry and stability of biphalin, a unique double-enkephalin analog, and its halogenated derivatives," J Pharmacol Exp Ther. Mar. 1996;276(3):1049-57.*
Witt et al., "Pharmacodynamic and Pharmacokinetic Characterization of Poly(Ethylene Glycol) Conjugation of Met-Enkephalin Analog [D-Pen$^2$, D-Pen$^5$]-enkephalin (DPDPE)," *Journal of Pharmacology and Experimental Therapeutics*, vol. 298, No. 2, Aug. 2001; pp. 848-856.
Kurihara, A. et al., "Epidermal Growth Factor Radiopharmaceuticals: 111In Chelation, Conjugation to a Blood Brain Barrier Delivery Vector via a Biotin-Polyethylene Linker, ...", Bioconjugate Chem., vol. 10, pp. 502-511, May 17, 1995.
Patel D. et al, "Peptide Targetting and Delivery across the Blood-Brain Barrier Utilizing Synthetic Triglyceride Esters: Design, Synthesis and Bioactivity," Bioconjugate Chem., vol. 8, pp. 434-441 (1997).
Pardridge, "Physiologic-bases strategies for protein drug delivery to the brain," *Journal of Controlled Release*, 39 pp. 281-286 (1996).
Brownlees et al., "Peptidases, Peptides, and the Mammalian Blood-Brain Barrier," *Journal of Neurochemistry*, vol. 60, No. 3, pp. 793-803 (1993).

(Continued)

*Primary Examiner* — Cecilia Tsang
*Assistant Examiner* — Thomas S Heard
(74) *Attorney, Agent, or Firm* — Susan T. Evans

(57) ABSTRACT

A substantially hydrophilic conjugate is provided having a peptide that is capable of passing the blood-brain barrier covalently linked to a water-soluble nonpeptidic polymer such as polyethylene glycol. The conjugate exhibits improved solubility and in vivo stability and is capable of passing the blood-brain barrier of an animal.

20 Claims, 6 Drawing Sheets

OTHER PUBLICATIONS

Friden, "Utilization of an endogenous cellular transport system for the delivery of therapeutics across the blood-brain barrier," *Journal of Controlled Release*, 46, pp. 117-128 (1996).

Pardridge et al., "Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration," *Pharmaceutical Research*, vol. 15, No. 4, pp. 576-582 (1998).

Kawasaki et al., "Amino Acids and Peptides. XIX. Preparation of Enkephalin-Poly(Ethylene Glycol) Hybrid and Evaluation of Its Analgesic Activity," *Chem Pharm Bull.*, 41(11)pp. 2053-2054 (1993).

Maeda et al., "Amino Acids and Peptides. XXII. Preparation and Antinociceptive Effect of [D-Ala$^2$]Leu-Enkephalin-Poly(Ethylene Glycol) Hybrid," *Chem Pharm Bull.*, 17(6) pp. 823-825 (1994).

Williams et al., "Passage of a δ-Opioid Receptor Selective Enkephalin, [D-Penicillamine$^{2,5}$] Enkephalin, Across the Blood-Brain and the Blood-Cerebrospinal Fluid Barriers," *J. of Neurochemistry*, vol. 66, No. 3, pp. 1289-1299 (1996).

Zalipsky, "Chemistry of polyethylene glycol conjugates with biologically active molecules," *Advanced Drug Delivery Review*, 16, pp. 157-182 (1995).

Zalipsky et al., "Copolymers of Lysine and Polyethylene Glycol: A New Family of Functionalized Drug Carriers," *Bioconjugate Chem.*, vol. 4, No. 1, pp. 54-62 (1993).

Hruby et al., "Recent Developments in the Design of Receptor Specific Opioid Peptides," *Medicinal Research Review*, vol. 9, No. 3, pp. 343-401 (1989).

Non-Final rejection in U.S. Appl. No. 10/354,683, dated May 3, 2007.

Amendment by Applicant to Non-Final Rejection in U.S. Appl. No. 10/354,683 dated Jan. 23, 2007.

Non-Final Rejection in U.S. Appl. No. 10/354,683, dated Aug. 23, 2006.

Amendment by Applicant to Non-Final Rejection in U.S. Appl. No. 10/354,683, dated May 18, 2006.

Non-Final Rejection in U.S. Appl. No. 10/354,683, dated Feb. 28, 2006.

Response to Election/Restriction filed in U.S. Appl. No. 10/354,683, dated Dec. 2, 2005.

Election/Restriction filed in U.S. Appl. No. 10/354,683, dated Nov. 22, 2005.

Preliminary Amendment by Applicant for U.S. Appl. No. 10/354,683, dated Jan. 30, 2003.

The Merck Index. 11$^{th}$ Edition,Budavari et al. Ed, 1989 p. 1264 and p. 1379.

Sakane et al., *Pharm Res.*, 14(8):1085-1091 (1997).

Weber et al., *J. Pharm. Exp. Ther.*, 259(3):1109-1117 (1991).

Shimohigashi et al., 297:333-335 abstract (pp. 1-2) (1982).

Enzon Pharmaceuticals Catalog, "Macromolecular Engineering Technologies," pp. 1-14 (2004).

Nektar Advanced PEGylation Catalog, "Polyethylene Glycol and Derivatives for Advanced PEGylation," pp. 1-21 (2003).

Nektar Advanced PEGylation Catalog, "Polyethylene Glycol and Derivatives for Advanced PEGylation," pp. 1-24 (2004).

Nektar Advanced PEGylation Catalog, "Polyethylene Glycol and Derivatives for Advanced PEGylation," pp. 1-30 (2005-2006).

NOF Corporation Catalog, "Peg Derivatives, Phospholipid and Drug Delivery Materials for Pharmaceuticals," 1: 2-46 (2003).

Polypure Products Catalog, Apr. 2005.

Quanta Biodesign Catalog, "Labeling, Derivatization and Crosslinking Reagents for Biological and Related Materials with dPEG," pp. 1-38, Mar. 12, 2004.

Quanta Biodesign Catalog, "Labeling, Derivatization and Crosslinking Reagents for Biological and Related Materials with dPEG," pp. 1-31, Nov. 5, 2004.

Quanta Biodesign Product Catalog, "Leading Innovator, Producer and Provider of Monodisperse Discrete PEG (dPEG) Derivatives," pp. 1-51, Nov. 17, 2005.

Shearwater Polymers, Inc., Catalog, , "Functionalized Biocompatible Polymers for Research Polyethylene Glycol and Derivatives," pp. 2-49 (Mar. 1995).

Shearwater Polymers, Inc., Catalog, "Functionalized Biocompatible Polymers for Research and Pharmaceuticals: Polyethylene Glycol and Derivatives," pp: 2-53 (1997-1998).

Shearwater Polymers, Inc., Catalog, "Functionalized Biocompatible Polymers for Research and Pharmaceuticals: Polyethylene Glycol and Derivatives," pp. 2-50 (2000).

Bryan, Jenny, "Crossing the Blood-Brain Barrier: Drug Delivery to the Brain is Still Elusive", *The Pharmaceutical Journal*, 273:475-476 (2004).

Jeffrey, Susan, "Manipulating the Blood-Brain Barrier-A Realistic Therapeutic Goal?", *Neurology Reviews.com, Clinical Trends and News in Neurology*, 8(7): 6 pages (2000).

Arap, et al., "Cancer Treatment by Targeted Drug Delivery to Tumor Vasculature in a Mouse Model," *Science* 279:377-380 (1998).

Berendsen, "A Glimpse of the Holy Grail," *Science* 282:642-643 (1998).

Messer, "Vasopressin and Oxytocin," Web Document Updated Apr. 3, 2000; http://www.neurosci.pharm.utoledo.edu/MBC3320/vasopressin.htm; 5 pages.

Nagey, et al., "Cytotoxic Analogs of Luteinizing Hormone-Containing Doxorubicin or 2-Pyrrolinodoxorubicin, A Derivative 500-1000 Times More Potent," *PNAS USA* 93:7269-7273 (1996).

Rudinger, "Characteristics of the Amino Acids as Components of a Peptide Hormone Sequence," JA Parsons, ed. pp. 1-7 (1976).

Sigma, "Designing Custom Peptides," http://www.sigma-genosys.com/peptide_design.asp, (1998).

Smilek, et al., "A Single Amino Acid Change in a Myelin Basic Protein Peptide Confers the Capacity to Prevent Rather than Induce Experimental Autoimmune Encephalomyelitis," *PNAS USA* 88:9633-9637 (1991).

Voet, et al., "Abnormal Hemoglobins," Biochemistry, 2$^{nd}$ ed., pp. 235-241 (1995).

Maeda, et al., "Amino Acids and Peptides. XXIV. Preparation and Antinociceptive Effect of [D-Ala2,(N-Me)Phe4]Enkephalin Analog-Poly(Ethylene Glycol) Hybrids," Chem. Pharm. Bull, vol. 42, No. 9, pp. 1859-1863, (1994).

Munson, et al., "Pharmacokinetics: Disposition and Metabolism of Drugs", Principles of Pharmacology Basic Concepts & Clinical Applications, Champman & Hall, Chapter 2, pp. 39-48, (1995).

PCT International Search Report corresponding to PCT Application No. PCT/US2000/41070 date of mailing Oct. 11, 2001.

PCT Written Opinion corresponding to PCT Application No. PCT/US2000/41070 date of mailing Oct. 29, 2001.

PCT International Preliminary Examination Report corresponding to PCT/US2000/41070 date of mailing Feb. 13, 2002.

PCT International Preliminary Examination Report corresponding to PCT Application No. PCT/US2000/41070 date of completion of this report May 16, 2002.

Australian Examiner's first report corresponding to Australian Patent Application No. 16312/01 dated Apr. 21, 2004.

Canadian Examination report corresponding to Canadian Patent Application No. 2,385,533 dated Dec. 13, 2005.

European Communication corresponding to European Patent Application No. 00 978 902.5 dated Jun. 4, 2004.

European Communication corresponding to European Patent Application No. 00 978 902.5 dated Aug. 24, 2005.

Japanese Official Action corresponding to Japanese Patent Application No. 2001-527830 mail date Jul. 21, 2006.

Korean Notice to Submit a Response corresponding to Korean Patent Application No. 2002-7003658 dated Feb. 13, 2004.

Korean Final Office Action corresponding to Korean Patent Application No. 2002-7003658 dated Feb. 15, 2005.

Korean Notice to Submit a Response corresponding to Korean Patent Application No. 10-2002-7003658 dated May 16, 2006.

* cited by examiner

Analgesia of mPEG2K-DPDPE in Mice (I.C.V)

Analgesia of mPEG2K-DPDPE in Mice (I.V.)

PEG MW Dependence on Biphalin Analgesia in Mice (I.V.)

Analgesia of mPEG2K-Biphalin Analogs

Analgesia of (mPEG2K)2-Biphalin in Rats at Various Doses

S.C. and I.M. Injection of Biphalin and PEG-Biphalin in Rats

POLYMER STABILIZED NEUROPEPTIDES

CROSS REFERENCE TO RELATED APPLICATIONS

This application is a continuation of application Ser. No. 09/678,997, filed Oct. 4, 2000, now abandoned which application claims the benefit of U.S. Provisional Application No. 60/166,589, filed Nov. 19, 1999, and claims the benefit of their earlier filing dates under 35 U.S.C. Section 119(e).

FIELD OF THE INVENTION

The invention relates to a conjugate between a peptide and polyethylene glycol or a substantially substitutable polymer and a method of use thereof.

BACKGROUND OF THE INVENTION

There has been significant progress in the discovery and development of potential neuropharmaceuticals (small molecules, peptides, proteins, and antisense) for treating pain and brain disorders such as Alzheimer's and Parkinson's diseases over the last decade. However, systemic delivery of many newly discovered neuropharmaceuticals has been hampered by the lack of an effective system for delivering them. Intravenous injection is usually ineffective because of inadequate transport across the barrier between the brain and the blood supply (the "blood-brain barrier" or "BBB"). The blood-brain barrier is a continuous physical barrier that separates the central nervous system, i.e., the brain tissue, from the general circulation of an animal. The barrier is comprised of microvascular endothelial cells that are joined together by complex tight intracellular junctions. This barrier allows the selective exchange of molecules between the brain and the blood, and prevents many hydrophilic drugs and peptides from entering into the brain. Many of the new potent neuroactive pharmaceuticals do not cross the BBB because they have a molecular weight above 500 daltons and are hydrophilic. Compounds that are non-lipophilic and have a molecular weight greater than 500 daltons generally do not cross the BBB.

Several strategies for delivering high molecular weight, non-lipophilic drugs to the brain have been developed including intracerebroventricular infusion, transplantation of genetically engineered cells that secrete the neuroactive compound, and implantation of a polymer matrix containing the pharmaceutical. See Pardridge, W. M., *J. Controlled Rel.*, (1996) 39:281-286. However, all of these involve invasive surgical procedures that can entail a variety of complications.

Four nonsurgical transport mechanisms have been identified for crossing the BBB, including: (i) transmembrane diffusion, (ii) receptor-mediated transport, (iii) absorptive-mediated endocytosis, and (iv) carrier-mediated transport. See Brownless et al., *J. Neurochemistry*, (1993) 60(3):793-803. Vascular permeability can be increased by opening the tight junctions with hyperosmotic saccharide solutions and analogs of bradykinin. An inherent problem in this method is that undesirable compounds in the general circulation may enter the brain through the artificially enlarged openings in the blood-brain barrier.

It has been discovered that capillary endothelial cells in the blood-brain barrier have a high level of receptors to transferrin, insulin, insulin-like growth factor I and II, low-density lipoprotein and atrial natriuretic factor. See Friden, P. M., *J. Controlled Rel.*, (1996) 46:117-128. U.S. Pat. No. 5,833,988 to Friden describes a method for delivering a neuropharmaceutical or diagnostic agent across the blood-brain barrier employing an antibody against the transferrin receptor. A nerve growth factor or a neurotrophic factor is conjugated to a transferrin receptor-specific antibody. The resulting conjugate is administered to an animal and is capable crossing the blood-brain barrier into the brain of the animal.

U.S. Pat. No. 4,902,505 to Pardridge et al. describes the use of chimeric peptides for neuropeptide delivery through the blood-brain barrier. A receptor-specific peptide is used to carry a neuroactive hydrophilic peptide through the BBB. The disclosed carrier proteins, which are capable of crossing the BBB by receptor-mediated transcytosis, include histone, insulin, transferrin, insulin-like growth factor I (IGF-I), insulin-like growth factor II (IGF-II), basic albumin, and prolactin. U.S. Pat. No. 5,442,043 to Fukuta et al. discloses using an insulin fragment as a carrier in a chimeric peptide for transporting a neuropeptide across the blood-brain barrier.

Non-invasive approaches for delivering neuropharmaceutical agents across the BBB are typically less effective than the invasive methods in actually getting the agent into the brain. High doses of the chimeric peptides are required to achieve the desired therapeutic effect because they are prone to degradation. The concentration of the chimeric peptides in the blood circulation can be quickly reduced by proteolysis. An aqueous delivery system is not generally effective for delivering hydrophobic drugs.

Another method for delivering hydrophilic compounds into the brain by receptor-mediated transcytosis is described by Pardridge et al. in *Pharm. Res.* (1998) 15(4):576-582. A monoclonal antibody to the transferrin receptor (OX26 MAb) modified with streptavidin is used to transport the cationic protein, brain-derived neurotrophic factor (BDNF) through the BBB. BDNF is first modified with $PEG^{2000}$-biotin to form $BDNF\text{-}PEG^{2000}$-biotin, which is then bound to the streptavidin-modified antibody OX26 MAb. The resulting conjugate was shown to be able to cross the BBB into the brain.

Enhancing the duration of antinociceptive effects in animals may result in less frequently administered analgesics, which can improve patient compliance and reduce potential side effects. Maeda et al. in *Chem. Pharm. Bull.* (1993) 41(11): 2053-2054, *Biol. Pharm Bull.* (1994) 17(6):823-825, and *Chem. Pharm. Bull.* (1994) 42(9):1859-1863 demonstrate that by attaching polyethylene glycol amine 4000 to the C-terminal leucine of Leu-enkephalin (distant from the tyrosine residue needed for antinociception), they could increase the potency and duration of Leu-enkaphalin when it was directly administered to the brain by intracerebroventricular injection.

There is a need in the art for an improved method to deliver neuroactive agents from the systemic circulation across the blood-brain barrier and into the brain that reduces or eliminates some of the drawbacks and disadvantages associated with the prior art.

SUMMARY OF THE INVENTION

This invention provides a method for delivering a peptide into the brain of a human or other animal through the blood-brain barrier. The peptide to be delivered is bonded to a water soluble, non-peptidic polymer to form a conjugate. The conjugate is then administered to an animal into the blood circulation so that the conjugate passes across the blood-brain barrier and into the brain. The water-soluble nonpeptidic polymer can be selected from the group consisting of polyethylene glycol and copolymers of polyethylene glycol and polypropylene glycol activated for conjugation by covalent attachment to the peptide.

In one embodiment of this invention, a substantially hydrophilic conjugate is provided having a transportable analgesic peptide, i.e., an analgesic peptide capable of passing the blood-brain barrier, covalently linked to a water-soluble, and nonpeptidic polymer such as polyethylene glycol. The conjugate is capable of passing the blood-brain barrier of an animal.

Suitable transportable peptides for use in this embodiment of the invention can include dynorphins, enkephalins, endorphins, endomorphins, and biphalin. Typically, these small neuropeptides are susceptible to degradation inside the body in blood circulation and in the brain. In contrast, when conjugated to polyethylene glycol or to a similar nonpeptidic, nonimmunogenic, water-soluble polymer having similar properties, these peptides exhibit significantly increased stability.

In another embodiment of this invention, a composition is provided comprising a conjugate as described above and a pharmaceutically acceptable carrier. The composition can be directly administered into the general circulation of an animal by any suitable means, e.g., parenteral injection, injection of intracerebral vein, and intranasal, pulmonary, ocular, and buccal administration.

In accordance with yet another embodiment of this invention, a method is provided for delivering an analgesic peptide across the blood-brain barrier into the brain of an animal. The method comprises providing a conjugate of this invention as described above, and administering the conjugate into the bloodstream of the host animal.

It has previously been considered that large hydrophilic polymers such as polyethylene glycol, when attached to a peptide that is capable of crossing the blood-brain barrier, would interfere with the transport of the peptide across the blood-brain barrier. In particular, it has been believed that direct conjugation of large hydrophilic polymers to a peptide not only would increase the hydrophilicity but would also impair the interaction between the peptide and its receptor or other structures in the BBB by steric interference from the large polymer strands.

It has now been discovered that, although the conjugate is substantially hydrophilic and contains a water-soluble and nonpeptidic polymer, the conjugate is nevertheless capable of passing the blood brain barrier of an animal. As compared to its native state, peptides conjugated to a water-soluble and non-peptidic polymer can exhibit reduced immunogenicity, enhanced water solubility, and increased stability. In particular, peptides conjugated to polyethylene glycol in accordance with this invention have a longer circulation time, reduced susceptibility to metabolic degradation and clearance, and once delivered into the brain through the blood-brain barrier, exhibit extended lifetime in the brain. Thus, this invention allows effective delivery of analgesic peptides into human and other animal brains and can significantly improve the efficacy of the peptides being delivered.

DETAILED DESCRIPTION OF THE INVENTION

Figure 1:
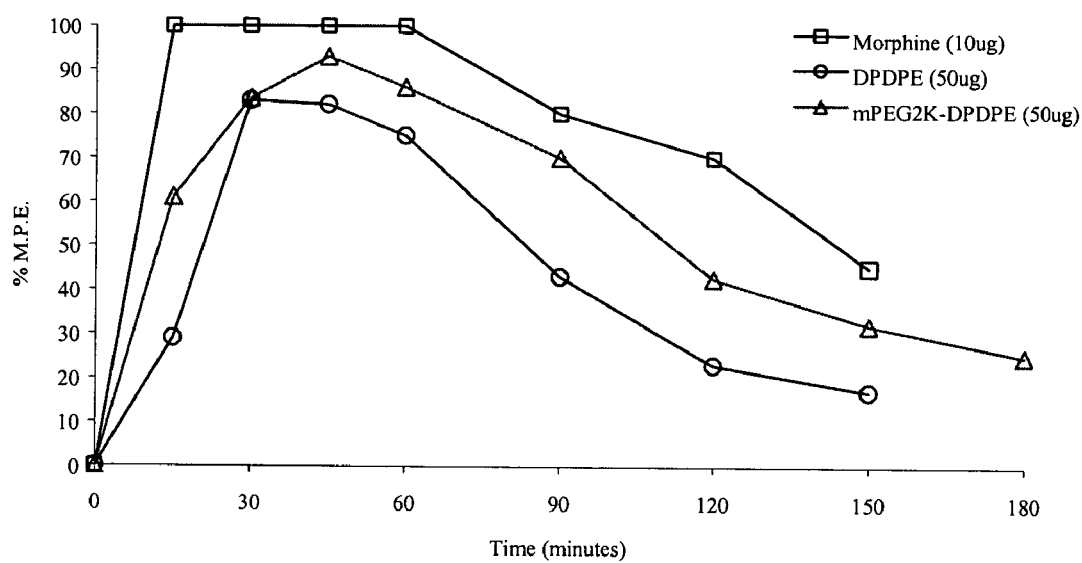
FIG. 1 is a plot showing the results of intracerebroventricular (i.c.v.) administration of an illustrative mPEG-2K-DPDPE conjugate (open triangles), morphine (open squares), and unmodified DPDPE (open circles) in male mice as described in Example 7. The results are plotted as percent maximum possible analgesic effect over time.

As used herein, "passing the blood-brain barrier" or "crossing the blood-brain barrier" means that, once administered into the blood circulation of an animal at a physiologically acceptable ordinary dosage, a conjugate or a peptide is capable of passing the blood-brain barrier of the animal to such a degree that a sufficient amount of the conjugate or peptide is delivered into the brain of the animal to exert a therapeutic, antinociceptive, or prophylactic effect on the brain, or to affect the biological functioning of the brain to a detectable degree. "Passing the blood-brain barrier" or "crossing the blood-brain barrier" can also be used herein to mean that the conjugate or peptide is capable of being taken up by an animal brain to a degree that is detectable by a suitable method known in the art, e.g., in situ brain perfusion as disclosed in Williams et al., *J. Neurochem.*, 66 (3), pp 1289-1299, 1996, which is incorporated herein by reference.

The conjugate of this invention normally is substantially hydrophilic. By the term "substantially hydrophilic," it is intended to mean that the conjugate of this invention does not contain a substantially lipophilic moiety such as fatty acids or glycolipids. Fatty acids and glycolipids are used in the art to increase the lipophilicity of a molecule in order to increase the ability of the molecule to pass cell membranes.

The term "analgesic" as used herein means any chemical substances that are desirable for delivery into the brain of humans or other animals for purposes of alleviating, mitigating, or preventing pain in humans or other animals, or otherwise enhancing physical or mental well being of humans or animals. Analgesic peptides can be introduced into the brain of an animal to exert a therapeutic, antinociceptive, or prophylactic effect on the biological functions of the animal brain, and can be used to treat or prevent pain.

Agents not typically considered "analgesic" can be attached to the peptide/polymer conjugate of the invention. For example, diagnostic or imaging agents can be attached to the conjugate. Fluorescein, proteins, or other types of agents specifically targeted to a particular type of cell or protein, such as monoclonal antibodies, can all be used in the conjugate of this invention for diagnostic or imaging purposes.

As described below, when an agent is incapable of passing the blood-brain barrier, i.e., is non-transportable across the BBB, then typically a peptide which is capable of passing the blood-brain barrier, i.e., is transportable across the BBB, will be used in a conjugate of this invention as a carrier.

In one embodiment of this invention, the peptide is a transportable analgesic peptide. As used herein, the term "transportable" means that the peptide is capable of crossing the blood-brain barrier of an animal as defined above. Thus, a conjugate is provided comprising a transportable peptide bonded to a water-soluble, nonpeptidic, nonimmunogenic polymer, including polyethylene glycol.

The term "peptide" means any polymerized α-amino acid sequence consisting from 2 to about 40 amino acids having a peptide bond (—CO—NH—) between each amino acid that can impact the condition and biological function of the brain of an animal. An analgesic peptide normally is an endogenous peptide naturally occurring in an animal, or fragments or analogs thereof. However, non-endogenous peptides that can impact the conditions and biological functions of animal brain are also included.

Many peptides are generally known in the art that are believed to be capable of passing the blood-brain barrier. Examples of transportable peptides that are believed to be capable of crossing the blood-brain barrier after PEGylation in accordance with the invention include, but are not limited to, biphalin and opioid peptides such as dynorphins, enkephalins, endorphins, endomorphins etc. Many derivatives and analogues of these transportable peptides can also be used in the practice of the invention.

Opioid peptides are believed to be especially suitable for practice of the invention. Opioid peptides exhibit a variety of pharmacological activities, including among them pain relief and analgesia.

Enkephalin is a pentapeptide having an amino acid sequence of H-Tyr-Gly-Gly-Phe-Met-OH (methionine enkephalin) or H-Tyr-Gly-Gly-Phe-Leu-OH (leucine enkephalin). Many enkephalin analogs have been identified and synthesized which are specific to different types of opiate receptors. See, e.g., Hruby and Gehrig, (1989) *Medicinal Research Reviews*, 9(3):343-401. For example, U.S. Pat. No. 4,518,711 discloses several enkephalin analogs including DPDPE, [D-Pen$^2$, D-Pen$^5$] enkephalin, which is a cyclic enkephalin analog made by substituting the second and fifth amino acid residues of the natural pentapeptides with either cysteine or with D- or L-penicillamine (beta, beta-dimethyl-cysteine) and joining the two positions by a disulfide bond. DPDPE has been shown to be able to pass the blood brain barrier into the brain. See, e.g., Williams et al. (1996) *Journal of Neurochemistry*, 66(3):1289-1299. U.S. Pat. No. 5,326,751 discloses DPADPE prepared by substituting the glycine residue at the third position of DPDPE with an alanine residue. Both of the patents are incorporated herein by reference.

Other enkephalin analogs include biphalin (H-Tyr-D-Ala-Gly-Phe-NH-)$_2$, which is a synthetic analog of enkephalin that is a dimerized tetramer produced by coupling two units having the formula H-Tyr-D-Ala-Gly-Phe-OH at the C- terminus with hydrazine. The dimeric form of enkephalin enhances affinity, and specificity to the delta-opioid receptor. Dimeric enkephalin analogs are disclosed in Rodbard et al. U.S. Pat. No. 4,468,383, the contents of which are incorporated herein by reference.

Dynorphins are another class of opioid peptides. Naturally isolated dynorphin has 17 amino acids. Many dynorphin fragments and analogs have been proposed in the art, including, e.g., dynorphin (1-10), dynorphin (1-13), dynorphin (1-13) amide, [D-Pro$^{10}$] Dynorphin (1-11) (DPDYN), dynorphin amide analogs, etc. See, e.g., U.S. Pat. Nos. 4,684,624, 4,62, 941, and 5,017,689, which are incorporated herein by reference. Although such analgesic peptides are capable of transporting across the blood-brain barrier, many of them have a very short half-life due to their susceptibility to biodegradation inside the body.

Even though polyethylene glycol normally has a large molecular weight and is hydrophilic, conjugation to the transportable peptides in the absence of a lipophilic moiety does not interfere with transportability of the peptides. The conjugated peptides remain capable of crossing the blood-brain barrier. Typically, upon administration into the general circulation of an animal, the conjugate of the invention, comprising a transportable peptide bonded to polyethylene glycol or an equivalent polymer, is taken up by the brain at a much greater percentage as compared to an unconjugated form of the peptide. The peptides in the conjugates of this invention have increased stability and exhibit extended half-life inside the body.

In another embodiment of this invention, a conjugate is provided comprising a first peptide, which is a transportable peptide, and a second neuroactive agent linked to each other by polyethylene glycol or an equivalent polymer. This second neuroactive agent may or may not be capable of crossing the blood-brain barrier by itself. The transportable peptide is used as a carrier to transport a non-transportable neuroactive agent across the blood-brain barrier into the brain of an animal. The linking polymer serves not only as a linker but also increases solubility and stability of the conjugate and reduces the immunogenicity of both the neuropeptide and the other neuroactive agent to be delivered.

In accordance with the invention, the transportable peptide and, optionally, another neuroactive agent as described above, are covalently linked to a water-soluble and nonpeptidic polymer to form a conjugate of this invention. The water-soluble and nonpeptidic polymers suitable for use in various aspects of this invention include polyethylene glycol, other polyalkylene glycols, and copolymers of polyethylene glycol and polypropylene glycol.

As used herein, the term polyethylene glycol ("PEG") is inclusive and means any of a series of polymers having the general formula:

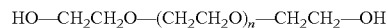

wherein n ranges from about 10 to 2,000. PEG also refers to the structural unit:

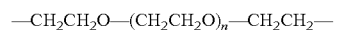

wherein n ranges from about 10 to about 2000. Thus, by PEG is meant modified PEGs including methoxy-PEGs; PEGs having at least one terminal moiety other than a hydroxyl group which is reactive with another moiety; branched PEGs; pendent PEGs; forked PEGs; and the like.

The polyethylene glycol useful in the practice of this invention normally has an average molecular weight of from about 200 to 100,000 daltons. Molecular weights of from about 200 to 10,000 are somewhat more commonly used. Molecular weights of from about 300 to 8,000, and in particular, from about 500 to about 5,000 daltons, are somewhat typical.

PEG is useful in biological applications because it has properties that are highly desirable and is generally approved for biological or biotechnical applications. PEG typically is clear, colorless, odorless, soluble in water, stable to heat, inert to many chemical agents, does not hydrolyze or deteriorate, and is generally nontoxic. Poly(ethylene glycol) is considered to be biocompatible, which is to say that PEG is capable of coexistence with living tissues or organisms without causing harm. More specifically, PEG, in itself, is normally considered nonimmunogenic, which is to say that PEG does not tend to produce an immune response in the body. Desirable terminal activating groups by which PEG can be attached to various peptides should not appreciably alter the nonimmunogenic character of the PEG, so as to avoid immunogenic effects. Desirable PEG conjugates tend not to produce a substantial immune response or cause clotting or other undesirable effects.

PEG is a highly hydrated random coil polymer that can shield proteins or peptides from enzymatic digestion, immune system molecules and cells, and can increase the hydrodynamic volume to slow reticuloendothelial system (RES) clearance. PEG is a useful polymer having the properties of water solubility as well as solubility in many organic solvents. The unique solubility properties of PEG allow conjugation (PEGylation) to certain compounds with low aqueous solubility, with the resulting conjugate being water-soluble. However, PEGylation, which is conjugating a PEG molecule to another molecule, is not without its difficulties. The effects of a particular PEG derivative are not necessarily predictable. The result depends on the specific interaction between a particular compound and the functional non-peptidic PEG polymer.

The polymer used in this invention normally can be linear or branched. Branched polymer backbones are generally known in the art. Typically, a branched polymer has a central core moiety and a plurality of linear polymer chains linked to the central core. PEG is commonly used in branched forms that can be prepared by addition of ethylene oxide to various polyols, such as glycerol, pentaerythritol and sorbitol. For example, the four-arm, branched PEG prepared from pentaerythritol is shown below:

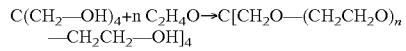

The central moiety can also be derived from several amino acids. An example is lysine.

The branched polyethylene glycols can be represented in general form as $R(\text{-PEG-OH})_n$, in which R represents the core moiety, such as glycerol or pentaerythritol, and n represents the number of arms. Suitable branched PEGs can be prepared in accordance with U.S. Pat. No. 5,932,462, the contents of which are incorporated herein in their entirety by reference. These branched PEGs can then be used in accordance with the teachings herein.

Forked PEGs and related polymers should be useful in the practice of the invention. The term "forked" is used to describe those PEGs that are branched adjacent at least one terminus thereof. The polymer has a branched moiety at one end of the polymer chain and two free reactive groups, one on each end of the branched moiety, for covalent attachment to another molecule. Each reactive moiety can have a tethering group, including, for example, an alkyl chain, linking a reactive group to the branched moiety. Thus, the branched terminus allows the polymer to react with two molecules to form conjugates. Forked PEGs and related forked polymers are described in copending, commonly owned U.S. patent application Ser. No. 09/265,989, which was filed Mar. 11, 1999 and is entitled Poly(ethylene glycol) Derivatives with Proximal Reactive Groups. This pending patent application is incorporated by reference herein in its entirety. The forked PEGs can be either linear or branched in the backbone attached to the branched terminus.

Water-soluble, substantially nonimmunogenic, nonpeptidic polymers other than PEG should also be suitable for practice of the invention, although not necessarily with equivalent results. These other polymers can be either in linear form or branched form, and include, but are not limited to, other poly(alkylene oxides), including copolymers of ethylene glycol and propylene glycol, and the like. Exemplary polymers are listed in U.S. Pat. No. 5,990,237, the contents of which are incorporated herein by reference in their entirety. The polymers can be homopolymers or random or block copolymers and terpolymers based on the monomers of the above polymers, straight chain or branched.

Specific examples of suitable additional polymers include, but are not limited to, poly(acryloylmorpholine) ("PAcM") and poly(vinylpyrrolidone)("PVP"), and poly(oxazoline). PVP and poly(oxazoline) are well known polymers in the art and their preparation should be readily apparent to the skilled artisan. PAcM and its synthesis and use are described in U.S. Pat. Nos. 5,629,384 and 5,631,322, the contents of which are incorporated herein by reference in their entirety.

To couple PEG to a peptide, e.g., a transportable peptide, to form a conjugate of this invention, it is often necessary to "activate" the PEG to prepare a derivative of the PEG having a reactive group at the terminus for reaction with certain moieties on the peptide. Many activated derivatives of PEG have been described in the art and can all be used in this invention, although not necessarily with equivalent results. An example of such an activated derivative is the succinimidyl succinate "active ester":

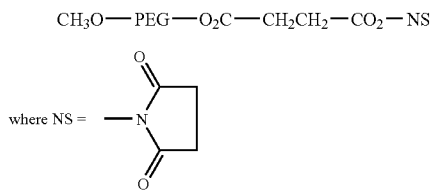

The succinimidyl active ester is a useful compound because it reacts rapidly with amino groups on proteins and other molecules to form an amide linkage (—CO—NH—). For example, U.S. Pat. No. 4,179,337 to Davis et al. describes coupling of this derivative to proteins (represented as PRO-NH$_2$):

Other activated PEG molecules known in the art include PEGs having a reactive cyanuric chloride moiety, succinimidyl carbonates of PEG, phenylcarbonates of PEG, imidazolyl formate derivatives of PEG, PEG-carboxymethyl azide, PEG-imidoesters, PEG-vinyl sulfone, active ethyl sulfone derivatives of PEG, tresylates of PEG, PEG-phenylglyoxal, PEGs activated with an aldehyde group, PEG-maleimides, PEGs with a terminal amino moiety, and others. These polyethylene glycol derivatives and methods for conjugating such derivatives to an agent are generally known in the art and are described in Zalipsky et al., *Use of Functionalized Poly(Ethylene Glycol)s for Modification of Polypeptides, in Use of Polyethylene Glycol Chemistry. Biotechnical and Biomedical Applications*, J. M. Harris, Ed., Plenum Press, New York (1992), and in Zalipsky, *Advanced Drug Reviews* (1995) 16:157-182, all of which are incorporated herein by reference.

Typically, conjugation of a water-soluble, nonimmunogenic polymer to a peptide in accordance with this invention results in the formation of a linkage between the polymer and the peptide. The term "linkage" is used herein to refer to groups or bonds normally formed as a result of a chemical reaction.

Covalent linkages formed in the practice of this invention can be hydrolytically stable. The linkage can be substantially stable in water and does not react with water at a useful pH, under physiological conditions, for an extended period of time, preferably indefinitely. Alternatively, the covalent linkage can also be hydrolytically degradable under physiological conditions so that the neuroactive agent can be released from the PEG in the body of an animal, preferably after it is delivered into the brain of the animal.

The approach in which drugs to be delivered are released by degradation of more complex agents under physiological conditions is a powerful component of drug delivery. See R. B. Greenwald, *Exp. Opin. Ther. Patents*, 7(6):601-609 (1997). For example, conjugates of the invention can be formed by attaching PEG to transportable peptides and/or neuroactive agents using linkages that are degradable under physiological conditions. The half-life of a PEG-neuroactive agent conjugate in vivo depends upon the type of reactive group of the PEG molecule that links the PEG to the neuroactive agent. Typically, ester linkages, formed by reaction of PEG carboxylic acids or activated PEG carboxylic acids with alcohol groups on neuroactive agents, hydrolyze under physiological conditions to release the neuroactive agent. See, e.g., S. Zalipsky, *Advanced Drug Delivery Reviews*, 16:157-182 (1995). For example, in PCT Publication No. WO 96/23794, it is disclosed that paclitaxel can be linked to PEG using ester linkages and the linked paclitaxel can be released in serum by hydrolysis. Antimalarial activity of dihydroartemisinin bonded to PEG through a hydrolyzable ester linkage has also been demonstrated. See Bentley et al., *Polymer Preprints*, 38(1):584 (1997). Other examples of suitable hydrolytically unstable linkages include carboxylate esters, phosphate esters, disulfides, acetals, imines, orthoesters, peptides and oligonucleotides.

Typically, the degradation rate of the conjugate should be controlled such that substantial degradation does not occur until the conjugate passes into the brain of an animal. Many peptides in their native state are subject to substantial degradation in blood circulation and in organs such as liver and kidney. The hydrolytically degradable linkages can be formed such that the half-life of the conjugate is longer than the time required for the circulation of the conjugate in the bloodstream to reach the blood-brain barrier. Some minor degree of experimentation may be required for determining the suitable hydrolytically unstable linkage between specific neuroactive agents and PEG derivatives, this being well within the capability of one skilled in the art once apprised of the present disclosure.

The covalent linkage between a peptide and a polymer can be formed by reacting a polymer derivative such as an activated PEG with an active moiety on the peptide. One or more PEG molecules can be linked to one peptide.

Conversely, multiple peptides, including transportable peptides and/or other types of neuroactive agents, can be linked to one PEG molecule. Typically, such a PEG molecule has multiple reactive moieties for reaction with the peptide and neuroactive agents. For this purpose, bifunctional PEGs, pendant PEGs, and dendritic PEGs can all be used. Reactive PEGs have also been synthesized in which several active functional groups are placed along the backbone of the polymer. For example, lysine-PEG conjugates have been prepared in the art in which a number of activated groups are placed along the backbone of the polymer. Zalipsky et al., *Bioconjugate Chemistry*, (1993) 4:54-62.

In one embodiment of this invention, a conjugate having a dumbbell structure is provided wherein a transportable peptide or other transportable neuroactive agent capable of passing the blood-brain barrier of an animal is covalently linked to one end of a polyethylene glycol molecule, and another neuroactive agent to be delivered into the brain of an animal is linked to the other end of the PEG molecule. This other neuroactive agent can be a transportable peptide, or any other neuroactive agent. Typically, it is not transportable and cannot in itself pass the blood-brain barrier. Therefore, the transportable peptide or other agent at one end of the PEG molecule acts as a carrier for delivering the non-transportable neuroactive agent into the brain. For this purpose, bifunctional PEGs, either homobifunctional or heterobifunctional PEGs, can be used. As used herein "bifunctional PEG" means a PEG derivative having two active moieties each being capable of reacting with an active moiety in another molecule. The two active moieties can be at two ends of a PEG chain, or proximate to each other at a forked end of a PEG chain molecule, allowing for steric hindrance, if any. Suitable transportable peptides for use in this invention are described above including, but not limited to, dynorphins, enkephalins, biphalin, endorphins, endomorphins, and derivatives and analogues thereof.

The conjugate of this invention can be administered to an animal for purposes of treating, mitigating, or alleviating pain. Examples of animal hosts include, but are not limited to, mammals such as humans, and domestic animals including cats, dogs, cows, horses, mice, and rats.

The conjugate of this invention can be administered in any suitable manner to an animal. For example, the conjugate can be administered parenterally by intravenous injection, intramuscular injection, or subcutaneous injection. Alternatively, the conjugate of this invention can also be introduced into the body by intranasal and pulmonary inhalation or by oral and buccal administration. Preferably, intravenous injection is utilized such that substantially all of the conjugate in an injection dose is delivered into the bloodstream of the animal, through which the conjugate circulates to the blood-brain barrier of the animal.

The conjugate can be injected in the form of any suitable type of formulation. For example, an injectable composition can be prepared by any known methods in the art containing the conjugate of this invention in a solvent such as water or solution, including saline, Ringer's solution. One or more pharmaceutically acceptable carriers that are compatible with the other ingredients in the formulation may also be added to the formulation. Excipients, including mannitol, sodium alginate, and carboxymethyl cellulose, can also be included. Other pharmaceutically acceptable components, including antiseptics such as phenylethylalcohol; stabilizers such as polyethylene glycol and albumin; isotonizing agents such as glycerol, sorbitol, and glucose; dissolution aids; stabilizing buffers such as sodium citrate, sodium acetate and sodium phosphate; preservatives such as benzyl alcohol; thickeners such as dextrose, and other commonly used additives can also be included in the formulations. The injectable formulation can also be prepared in a solid form such as lyophilized form.

The PEGylated transportable peptides of the invention can be administered in a variety of formulations, including, for example, intranasal, buccal, and oral administration. The dosage of the conjugate administered to a human or other animal will vary depending on the animal host, the types of transportable peptides and/or neuroactive agents used, the means of administration, and the symptoms suffered by the animal.

However, the suitable dosage ranges in a specific situation should be readily determinable by a skilled artisan without undue experimentation.

The invention is further illustrated by the following examples, which are intended only for illustration purposes and should not be considered in anyway to limit the invention.

EXAMPLE 1

Modification and Purification PEG-Dynorphin A

Dynorphin A (1-11) (H-Tyr-Gly-Gly-Phe-Leu-Arg-Arg-Ile-Arg-Pro-Lys-NH$_2$) (1.47 mg) was dissolved in 0.25 ml deionized water and 0.25 ml of 25mM NaP, pH 5.8 buffer in a 1.5 ml microcentrifuge tube. The reagent, NHS-PEG$_{2K}$-Fluoroscein (1.0 mg), was added to the peptide solution in approximately 2-fold mole excess. After 30 minutes of reaction time, 0.1 ml of 25 mM sodium phosphate buffer, pH 7.4 was added and the reaction was allowed to proceed at room temperature for 3 hours.

Conjugation of NHS-PEG$_{2K}$-Fluoroscein was monitored by capillary electrophoresis (CE) and mass spectrometry (MALDI). Purification of the PEG-Dynorphin A conjugate was performed on a HiTrap SP cation exchange column from Amersham/Pharmacia using a gradient elution from 5 mM sodium phosphate buffer, pH 4.0 to 50 mM sodium phosphate, 1.5M NaCl buffer, pH 7.5 in 53 minutes. Fractions were collected and the contents were analyzed by MALDI. These fractions were pooled and stored frozen prior to in vivo assay.

EXAMPLE 2

Modification and Purification PEG-Endomorphin II

Endomorphin II (H-Tyr-Pro-Phe-Phe-NH$_2$, 2.3 mg) was dissolved in 1.15 ml of 5 mM sodium phosphate buffer, pH 8.0. Modification of endomorphin II was performed in 1.5 hours at room temperature by adding mPEG$_{2000}$-SPA (38 mg) (mPEG succinimidyl propionate, MW 2,000) in a 5-fold molar excess. The reaction mixture was analyzed by mass spectrometry (MALDI) to determine the extent of modification. MALDI was used to verify that the reaction between mPEG$_{2000}$-SPA and endomorphin II went to completion. The sample was dialyzed against water using a 2000 MWCO membrane and lyophilized prior to in vivo assay.

EXAMPLE 3

In Situ Perfusion, Capillary Depletion, Brain Extraction and Protein Binding Studies of PEG-Dynorphin A and PEG-Endomorphin II The protocol for the rat brain perfusion experiments was approved by the Institutional Animal Care and Use Committee at the University of Arizona. The in situ perfusion, capillary depletion, brain extract and protein binding studies were carried out as previously reported (Williams et al., *J. Neurochem.*, 66 (3), pp1289-1299, 1996). PEG-dynorphin A (PdynA) had a very high in situ uptake R$_{Br}$ value of 0.343±1.84. In contrast in situ perfusion with I$^{125}$ Dynorphin, gave a very high R$_{Br}$ of approximately 0.96. The entire radioactivity was recovered in the solvent front of the subsequent HPLC, showing that labeled dynorphin A (1-11) rapidly degrades, probably to I$^{125}$Tyr.

Capillary depletion studies of the PdynA were carried out, and revealed that approximately 88% of the radioactivity associated with the capillary fraction rather than the brain parenchyma.

In situ uptake of PEG-endomorphin II (Pend) gave an R$_{Br}$ value of 0.057±0.008, similar to those previously reported for peptides. Subsequent capillary depletion showed that of the radioactivity entering the brain, 32% was associated with the capillary fraction with 67% in the brain parenchyma.

The protein binding of Pend was studied using the centrifree filter system. It was found that 30% of 25,000 dpm Pend was bound to a 1% BSA solution.

The major contribution is that PEGylation improved brain and blood enzymatic stability dramatically. Endomorphin and dynorphin are very unstable in either brain or blood with half-lives on the order of minutes. After PEGylation, those half-lives increased to hours for endomorphin II. In the case of endomorphin II, the half-life in blood plasma was 3.2 minutes, and brain tissue was 13 minutes. After PEGylation, those half-lives increased to greater than two hours.

EXAMPLE 4

Conjugation of PEG-Doxorubicin to Endomorphin I

Endomorphin I (H-Tyr-Pro-Trp-Phe-NH$_2$, 3.0 mg, 4.9E-6 moles) was dissolved in 1 ml of 50 mM sodium phosphate, pH 8.2 buffer containing 150 mM NaCl and 50 mM DTT. A four fold molar excess of Traut's reagent (2.7 mg) was added and was allowed to react at room temperature for 2 hours. The thiol-modified endomorphin was purified from DTT and Traut's reagent using a Superdex 30 size exclusion column (Pharmacia). The modified endomorphin fractions were collected and lyophilized.

Doxorubicin hydrochloride (3.0 mg, 5.2E-6 moles) was dissolved in 1.0 ml of 50 mM sodium phosphate, pH 7.2 buffer containing 150 mM NaCl. The pH of the solution was titrated to 8.0 with 0.1N sodium hydroxide. A ten-fold molar excess of heterobifunctional PEG (NHS-PEG$_{2K}$-OPSS), NHS-PEG$_{2K}$-orthpyridyldisulfide was added to the doxorubicin solution. The reaction was allowed to proceed at room temperature for 2 hours. OPSS-PEG$_{2K}$-doxorubicin was purified from unreacted PEG and free doxorubicin using a Superdex 30 size exclusion column. The OPSS-PEG$_{2K}$-doxorubicin fractions were collected and lyophilized.

The lyophilized powders of modified endomorphin I and OPSS-PEG$_{2K}$-doxorubicin were reconstituted in 50 mM sodium phosphate buffer, pH 6.0. An equimolar amount of each solution was mixed together and the two were reacted at room temperature for 6 hours. The doxorubicin-PEG$_{2K}$-endomorphin conjugate was purified on a Superdex 30 size exclusion column.

EXAMPLE 5

Conjugation of PEG to DPDPE 3.0 mg of DPDPE (Tyr-D-Pen-Gly-Phe-D-Pen) was dissolved in 5 ml of anhydrous acetonitrile. A 20% molar excess of PEG reagent (either mPEG-SPA 5K [27.9 mg] or mPEG-SPA 2K [11.1 mg]) and triethylamine (0.8µl) was added to the DPDPE. The reaction was allowed to proceed at room temperature under an argon atmosphere for 2 days. The sample was diluted to 15 ml with deionized water and lyophilized. The PEG-DPDPE powder was reconstituted in 5 ml of deionized water and purified on a Superdex 30 size exclusion column. The pertinent fractions were pooled together, dialyzed against water and frozen until in situ perfusion experiments.

Both $PEG_{2k}$-DPDPE and $PEG_{5k}$-DPDPE were iodinated and tested in in situ perfusion, capillary depletion, brain extraction and protein binding studies as in Example 3. A significant increase in brain uptake was observed for both $PEG_{2k}$-DPDPE and $PEG_{5k}$-DPDPE. It was determined that for both of these compounds, the increase in uptake was due to peptide entering the brain rather than being trapped in the capillaries.

EXAMPLE 6

Conjugation of PEG to Biphalin a. $(mPEG_{2K})_2$-Biphalin

Biphalin (21.1 mg, 0.046 mmol) was dissolved into 15 ml of anhydrous acetonitrile and treated with 16 µl of triethylamine (0.115 mmol, 2.5 fold molar excess). At the same time, $mPEG_{2K}$-SPA (10 mg, 0.055 mmol, 1.2 fold molar excess) was dissolved into 5 ml of acetonitrile. The dissolved $mPEG_{2K}$-SPA was slowly added into the above biphalin solution and the reaction mixture was stirred 66 hours at room temperature under nitrogen atmosphere.

Di-pegylated [$(mPEG_{2K})_2$-biphalin] and monopegylated biphalin [$mPEG_{2K}$-biphalin] were separated from unreacted PEG and free biphalin on a Vydac C18 reverse-phase column at 1 ml/min and 215 nm UV detector using a gradient elution of 30% to 60% solvent B. Solvent A is 0.1% TFA in water and solvent B is 0.1% TFA in acetonitrile.

b. $(mPEG_{5K})_2$-Biphalin 118.7 mg of methoxy-$PEG_{5K}$-SPA ($2.374 \times 10^{-5}$ moles, 1.5 fold molar excess) was dissolved in 3.0 mL anhydrous acetonitrile. Under a slow argon flow, 10.0 mg of biphalin ($1.583 \times 10^{-5}$ moles of —$NH_2$ group) was added, followed by pipette addition of 4.4 µL triethylamine ($3.166 \times 10^{-5}$ moles, 2.0 fold molar excess) into the solution. The solution was stirred at ambient overnight.

The solvent was evaporated via rotary evaporator at 40° C. to near dryness, then further dried under high vacuum for 5 minutes. The residue was then dissolved in 10 mL deionized water. The solution pH was 4.5. The solution was loaded by injection into a prehydrated Slide-A-Lyzer dialysis cassette with 3500 MWCO (from PIERCE) and then dialyzed against 2×900 mL deionized water over three days.

The solution was loaded onto a 2 mL DEAE Sepharose column, and the eluent was collected. The column was eluted with an additional 125 mL of deionized water, and the eluent (pH7.6) was collected. The two fractions were combined, the solution was frozen in liquid nitrogen, and then lyophilized.

c. $(mPEG_{12K})_2$-Biphalin 141.4 mg Methoxy-$PEG_{12K}$-SPA ($1.187 \times 10^{-5}$ moles, 1.5 fold molar excess) was dissolved in 2.0 mL of anhydrous acetonitrile. Under a slow argon flow, 5.0 mg of biphalin2TFA ($7.915 \times 10^{-6}$ moles of —$NH_2$ group) was added, followed by pipette addition of 2.2 µL of triethylamine ($1.583 \times 10^{-5}$ moles, 2.0 fold molar excess) into the solution. The solution was stirred at ambient overnight.

The solvent was evaporated under high vacuum at room temperature to dryness. The residue was then dissolved in 10 mL deionized water. The solution was loaded by injection into a prehydrated Dialysis Cassette with 10000 MWCO (from PIERCE) and dialyzed against 2×800 mL deionized water over three days.

The solution was diluted to a volume of 18 mL by addition of deionized water. The solution was loaded onto 10 mL DEAE Sepharose column, and the eluent was collected. The column was eluted with an additional 90 mL of deionized water. The fractions were then combined, frozen in liquid nitrogen, and then lyophilized.

d. $(mPEG_{20K})_2$-Biphalin 255.2 mg Methoxy-$PEG_{20K}$-SPA ($1.187 \times 10^{-5}$ moles, 1.5 fold molar excess) was dissolved in 3.0 mL anhydrous acetonitrile. Under a slow argon flow, 5.0 mg biphalin2TFA ($7.915 \times 10^{-6}$ moles of —$NH_2$ group) was added, followed by pipette addition of 2.2 µL triethylamine ($1.583 \times 10^{-5}$ moles, 2.0 fold molar excess) into the solution. The solution was stirred at ambient overnight.

The solvent was evaporated under high vacuum at room temperature until dryness. The residue was dissolved in 10 mL deionized water. The solution was loaded by injection into a prehydrated Dialysis Cassette with 10000 MWCO (from PIERCE) and dialyzed against 2×800 mL deionized water over three days.

The solution was diluted to a volume of 25 mL by addition of deionized water, and loaded onto a 15 mL DEAE Sepharose column. The eluent was collected, and the column eluted with an additional 150 mL of deionized water. The fractions were combined, frozen under liquid nitrogen, and then lyophilized.

Purity of each sample was determined by reverse-phase HPLC and by mass spectrometry (MALDI).

EXAMPLE 7

Analgesia Assay

Animals

Male ICR mice (20-25 g) or male Sprague-Dawley rats (250-300 g) (Harlan Sprague-Dawley Inc., Indianapolis, Ind.) were used for these experiments. Animals were housed four per cage in an animal care facility maintained at 22±0.5° C. with an alternating 12 hr light-dark cycle. Food and water were available ad libitum. Animals were used only once.

Protocol

All drugs were dissolved in sterile saline and were prepared so that the proper dose would be delivered in 5 µl (i.c.v.), 100 µl (i.v.), 100 µl (s.c.) and 100 µl (i.m.) of the vehicle. All rodents were recorded for baseline latency before injection of the drug. A morphine control was used with the i.c.v. and i.v. injection procedures to compare the analgesic efficacies of test compounds.

I.C.V. Injection

Rodents were placed into a jar containing gauze soaked with ethyl ether until they went into a light sleep. The rodents were immediately removed from the jar and a ½" incision was made with a scalpel to expose the top of the skull. The right lateral ventricle was located by measuring 2 mm lateral of the midline and 2 mm caudal to Bregma. At this point, a Hamilton syringe (22G, ½") was placed through the skull 2 mm and a 5 µl injection of the compound was delivered. The rodents were then placed back into their cages until the specified testing time. Methylene blue was placed into the injection site to insure proper delivery of the compound into the lateral ventricle.

I.V. Injection

Rodents were placed into a restraint holder and their tails were placed into a beaker of warm water and then swabbed with ethanol to maximize vasodilation in the tail veins. A vein was selected and the restraint was braced to prevent excessive movement. A 30G needle was selected as the proper size for delivery of the compounds. The needle was carefully inserted into the vein of each mouse and a 100 μl bolus was slowly delivered. Blanching of the vein up towards the body was indicative of proper delivery.

S.C. Injection

Rats were restrained by hand to prevent excessive movement. A 30G needles was selected as the proper size for delivery of the compounds. The needle was carefully inserted into the scruff of the neck of each rat and a 100 μl bolus was slowly delivered.

I.M. Injection

Rats were restrained by hand to prevent excessive movement. A 30G needles was selected as the proper size for delivery of the compounds. The needle was carefully inserted into the right hind leg muscle of each rat and a 100 μl bolus was slowly delivered.

Analgesia Testing

The rodents were placed into restraint holders and their tails were properly placed under the radiant heat beam. The beam was turned on and the time until the animal flicked their tail from under the beam was recorded at each time point. In instances where the animals moved their tails without a flick, the animals were retested only if the elapsed time under the radiant beam was less than 5 seconds.

Assessment of Analgesic Data

The raw data (recorded times) was converted to a percentage of the maximum possible effect (% M.P.E.) which was determined as 15 seconds. % M.P.E. was determined by the following equation:

$$\% \text{ M.P.E.} = (\text{Recorded time} - \text{Baseline})/(15 - \text{Baseline}) \times 100$$

These percentages then allow the compound to be plotted according to % M.P.E. vs. Time. The curve can then be analyzed to determine the area under the curve (AUC).

The results of the i.c.v. administration of the PEG-DPDPE clearly indicates that PEGylation does not interfere with DPDPE's ability to produce an analgesic effect. (FIG. 1) Furthermore, the study showed a trend toward a prolongation of analgesic effect of the PEGylated compound when compared to the parent compound.

Figure 2:
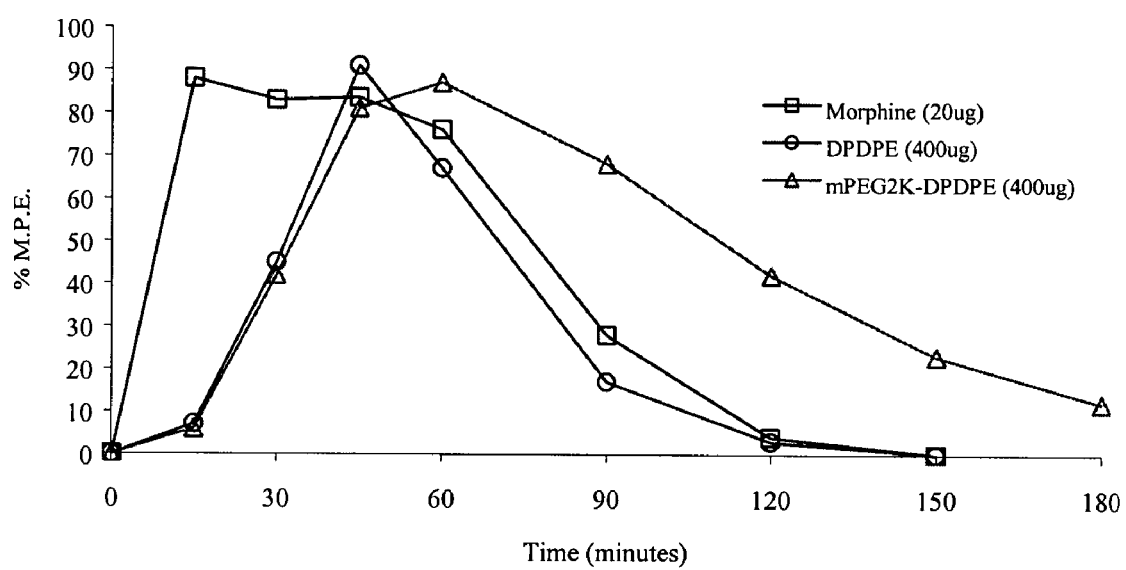
FIG. 2 is a plot showing the results of intravenous administration of an illustrative mPEG-2K-DPDPE conjugate (open triangles), morphine (open squares), and unmodified DPDPE (open circles) in male mice as described in Example 7. The results are plotted as percent maximum possible analgesic effect over time.

Intravenous injection of PEG-DPDPE showed that the PEGylated compound is able to cross the blood brain barrier, in sufficient amounts, as to maintain its analgesic properties. (FIG. 2) This study also helped confirm that PEGylation for DPDPE significantly prolongs the duration of the analgesic effect.

Figure 3:
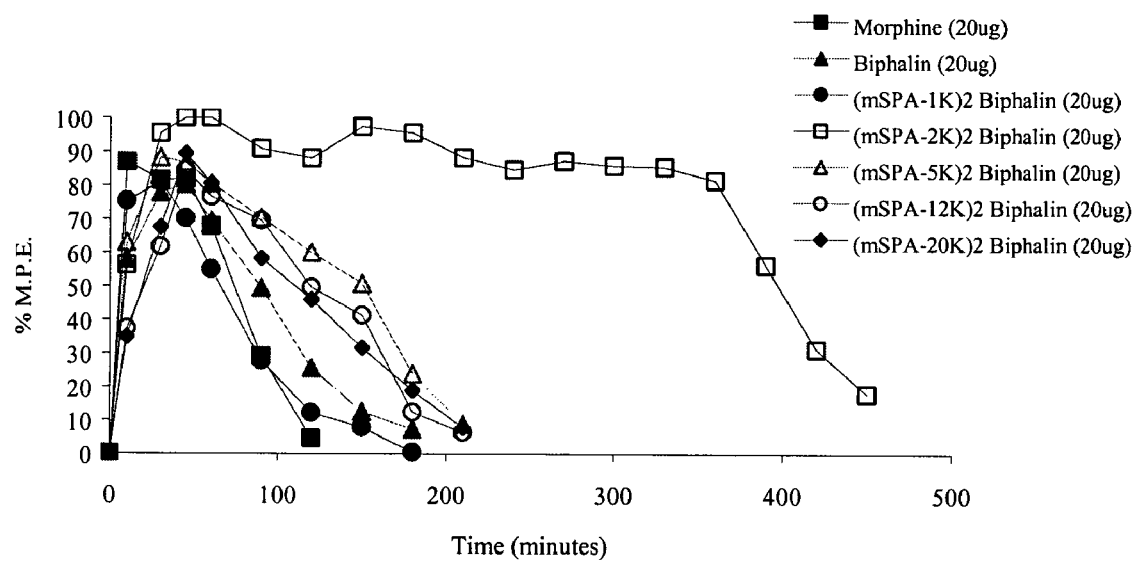
FIG. 3 is a plot showing the analgesic effect of five di-PEGylated biphalin conjugates of varying molecular weights compared to morphine and unmodified biphalin when administered intravenously in male mice as described in Example 7. The results are plotted as percent maximum possible analgesic effect over time.

All PEGylated biphalin and biphalin samples exhibited a potent analgesic response in mice with a maximum response of 80-90% reached between 30-45 minutes. The $(\text{mPEG}_{2K})_2$-biphalin continued to prolong the analgesic effect with a 50% M.P.E. being seen at the 400 minute mark of the study as compared to the 90 minute mark for native biphalin. The data also shows an inverse relationship between the molecular weight of PEG and the % M.P.E. (FIG. 3)

Figure 4:
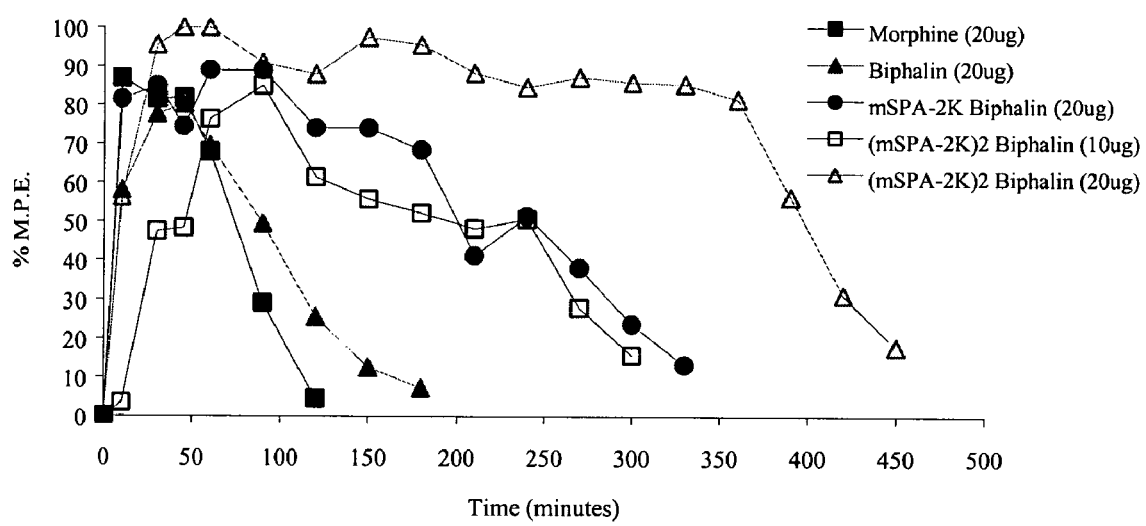
FIG. 4 is a plot comparing the analgesic effect of an illustrative diPEGylated biphalin conjugate, an illustrative mono-PEGylated biphalin conjugate, morphine and unmodified biphalin, when administered intravenously in male mice as described in Example 7. The results are plotted as percent maximum possible analgesic effect over time.

When comparing the analgesic effect of monopegylated biphalin ($\text{mPEG}_{2K}$-biphalin) to that of the dipegylated biphalin [$(\text{mPEG}_{2K})_2$-biphalin] at the same concentration in mice, the duration of analgesic effect for $\text{mPEG}_{2K}$-biphalin is nearly half of that for $(\text{mPEG}_{2K})_2$-biphalin at 50% M.P.E. (FIG. 4) In fact there is nearly equivalent analgesic effect of $\text{mPEG}_{2K}$-biphalin at half the dose of $(\text{mPEG}_{2K})_2$-biphalin.

Figure 5:
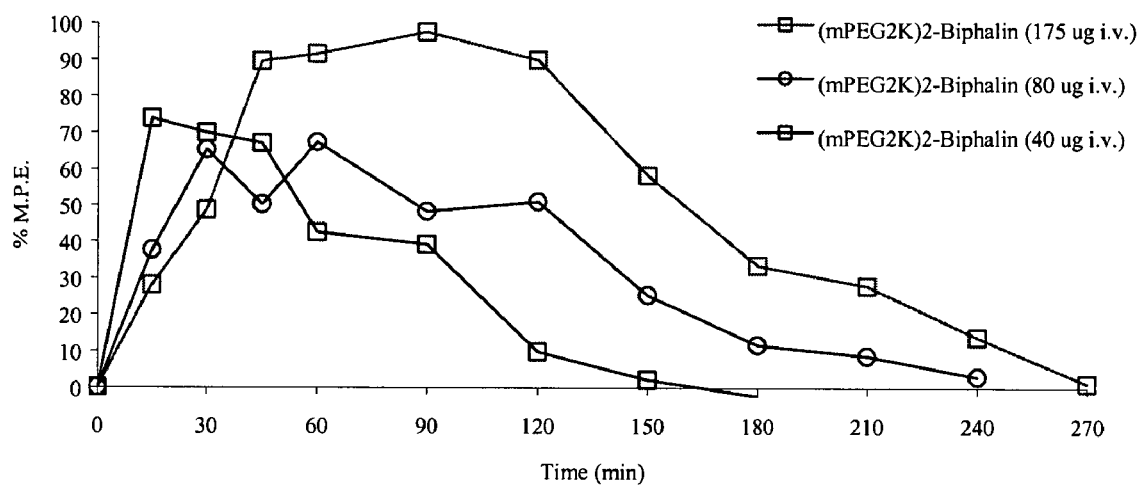
FIG. 5 is a plot comparing the analgesic effect of various doses of an exemplary diPEGylated biphalin conjugate when administered intravenously to male rats as described in Example 7. Results are plotted as percent maximum possible analgesic effect over time.
Figure 6:
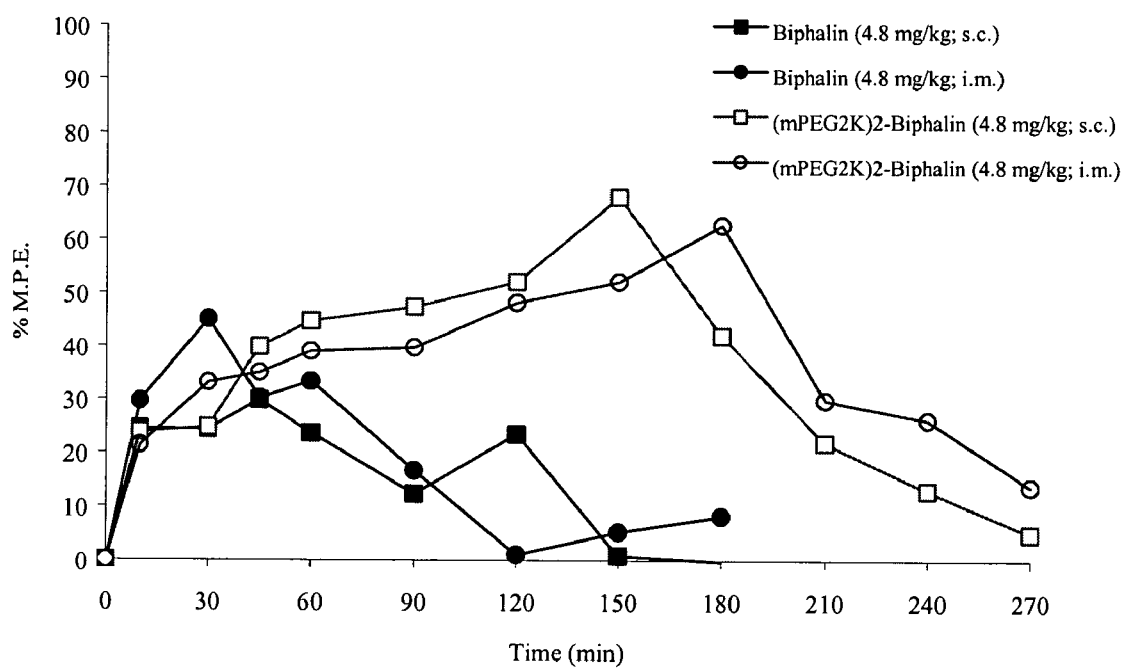
FIG. 6 is a plot comparing the analgesic effect of an illustrative diPEGylated biphalin conjugate to unmodified biphalin when administered to male rats by both subcutaneous and intramuscular injection.

Intravenous administration of $(\text{mPEG}_{2K})_2$-biphalin gives a longer lasting analgesic effect in rats than native biphalin at the various doses tested. (FIG. 5) Rats given $(\text{mPEG}_{2K})_2$-biphalin by subcutaneous or intramuscular administration show elevated and sustained levels of analgesic activity as compared to native biphalin at the same concentration. (FIG. 6)

EXAMPLE 8

In Situ Perfusion Studies of PEG-DPDPE and PEG-Biphalin

The protocol for the rat brain perfusion experiments was approved by the Institutional Animal Care and Use Committee at the University of Arizona. The in situ perfusion studies were carried out as previously reported (Williams et al., *J. Neurochem.*, 66 (3), pp1289-1299, 1996). $\text{PEG}_{2K}$-DPDPE had a very high in situ uptake $R_{Br}$ value of 3.41±0.15. The in situ perfusion of $I^{125}$ DPDPE is comparable to that of the monopegylated DPDPE, $R_{Br}$=3.54±0.30. $I^{125}$ labeled Biphalin has an in situ perfusion uptake of 7.26±0.11, while the in situ uptake of $(\text{mPEG}_{2K})_2$-Biphalin was dramatically lower, $R_{Br}$ value of 2.70±0.27.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A hydrophilic polymer-peptide conjugate consisting of a peptide that is either biphalin or [D-Pen$^2$, D-Pen$^5$] enkephalin (DPDPE) covalently linked to one or more water-soluble polymer chains having a molecular weight from about 2,000 to about 100,000 daltons and selected from either poly(ethylene glycol) or copolymers of ethylene glycol and propylene glycol, wherein said conjugate, when administered into the blood circulation of a mammal, is capable of transport across the blood brain barrier.

2. The conjugate of claim 1, which, when administered to the blood circulation of a mammal, has an extended duration of analgesic effect when compared to the corresponding unconjugated peptide.

3. The conjugate of claim 1, wherein said one or more water soluble polymer chains is absent one or more lipophilic moieties.

4. The conjugate of claim 1, wherein said peptide is covalently linked to at least one terminus of said one or more polymer chains.

5. The conjugate of claim 1, wherein said peptide is covalently linked at an N-terminus to said one or more polymer chains.

6. The conjugate of claim 1, wherein said water-soluble, polymer chain is a copolymer of polyethylene glycol and polypropylene glycol.

7. The conjugate of claim 1, wherein said water-soluble polymer chain is polyethylene glycol.

8. The conjugate of claim 7, wherein said polyethylene glycol is selected from the group consisting of monomethoxypolyethylene glycol, branched polyethylene glycol, polyethylene glycol with degradable linkages in the backbone, homobifunctional polyethylene glycol, heterobifunctional polyethylene glycol, multi-arm polyethylene glycol, pendant polyethylene glycol, and forked polyethylene glycol.

9. The conjugate of claim 1, wherein said peptide is conjugated to a single polyethylene glycol chain.

10. The conjugate of claim 1, comprising biphalin covalently attached to two polyethylene glycol chains.

11. The conjugate of claim 1, wherein said polymer chain is polyethylene glycol having a nominal average molecular weight of about 2,000 daltons to about 40,000 daltons.

12. The conjugate of claim 11, wherein said polyethylene glycol has a nominal average molecular weight selected from the group consisting of 2000 daltons, 5000 daltons, 8,000 daltons, 10,000 daltons, 12,000 daltons and 20,000 daltons.

13. The conjugate of claim 11, wherein said polyethylene glycol has a nominal average molecular weight of 2,000 daltons.

14. A pharmaceutical composition comprising a conjugate according to claim 1 and a pharmaceutically acceptable carrier.

15. The conjugate of claim 7, wherein said polymer chain is linear.

16. The conjugate of claim 1, wherein said peptide is covalently linked to said one or more water soluble polymer chains at a tyrosine residue of said peptide.

17. The conjugate of claim 1, wherein said peptide is biphalin.

18. The conjugate of claim 1, wherein said peptide is DPDPE.

19. The conjugate of claim 1, wherein said polymer chain is absent fatty acids and glycolipids.

20. The conjugate of claim 1, wherein said polymer chain is monomethoxypolyethylene glycol.

* * * * *